United States Patent
Schneider

(10) Patent No.: US 12,369,993 B2
(45) Date of Patent: Jul. 29, 2025

(54) INSTRUMENT, MAGNETIC RESONANCE TOMOGRAPHY SYSTEM AND METHOD FOR TRACKING THE INSTRUMENT

(71) Applicant: Siemens Healthcare GmbH, Erlangen (DE)

(72) Inventor: Rainer Schneider, Höchstadt (DE)

(73) Assignee: Siemens Healthineers AG, Forchheim (DE)

( * ) Notice: Subject to any disclaimer, the term of this patent is extended or adjusted under 35 U.S.C. 154(b) by 91 days.

(21) Appl. No.: 18/080,912

(22) Filed: Dec. 14, 2022

(65) Prior Publication Data

US 2023/0190385 A1 Jun. 22, 2023

(30) Foreign Application Priority Data

Dec. 20, 2021 (EP) .................................. 21216119

(51) Int. Cl.
*A61B 34/20* (2016.01)

(52) U.S. Cl.
CPC ...... *A61B 34/20* (2016.02); *A61B 2034/2051* (2016.02); *A61B 2034/2055* (2016.02); *A61B 2034/2072* (2016.02)

(58) Field of Classification Search
None
See application file for complete search history.

(56) References Cited

U.S. PATENT DOCUMENTS

| | | | | |
|---|---|---|---|---|
| 6,236,205 B1 * | 5/2001 | Ludeke | ............... | G01R 33/285 324/318 |
| 2007/0043288 A1 * | 2/2007 | Mueller | ............... | G01R 33/287 600/411 |
| 2007/0080686 A1 | 4/2007 | Dumoulin | | |
| 2009/0281419 A1 * | 11/2009 | Troesken | ............... | A61B 90/36 342/450 |
| 2010/0244831 A1 * | 9/2010 | Elgort | ................. | G01R 33/287 324/309 |
| 2016/0324424 A1 * | 11/2016 | Hengerer | ............ | G01R 33/287 |
| 2017/0108569 A1 | 4/2017 | Harvey | | |
| 2020/0249292 A1 * | 8/2020 | Biber | ................ | G01R 33/3854 |

FOREIGN PATENT DOCUMENTS

DE 19755782 A1 6/1999
EP 3467531 A1 4/2019

* cited by examiner

*Primary Examiner* — Katherine L Fernandez
(74) *Attorney, Agent, or Firm* — Lempia Summerfield Katz LLC

(57) ABSTRACT

An instrument, a magnetic resonance tomography system and a method for detecting a relative position of the instrument in relation to the magnetic resonance tomography system. An encoded locator signal in a frequency range of the magnetic resonance tomography system is emitted by a transponder on the instrument, received by a plurality of sensors disposed on the magnetic resonance tomography system and a relative position of the transponder in relation to the sensors is determined by the locator signal detected by the sensors.

7 Claims, 2 Drawing Sheets

INSTRUMENT, MAGNETIC RESONANCE TOMOGRAPHY SYSTEM AND METHOD FOR TRACKING THE INSTRUMENT

CROSS REFERENCE TO RELATED APPLICATIONS

This application claims the benefit of EP21216119.4, filed on Dec. 20, 2021, which is hereby incorporated by reference in its entirety.

FIELD

Embodiments relate to an instrument, a magnetic resonance tomography system, and a method for operating the magnetic resonance tomography system in which the relative position of an instrument in relation to the magnetic resonance tomography system is determined.

BACKGROUND

Magnetic resonance tomography systems are imaging devices that, in order to image an examination subject, align nuclear spins of the examination subject by a strong external magnetic field and excite them into precession around the alignment by an alternating magnetic field. The precession or return of the spins from the excited state into a state having lower energy in turn generates as response an alternating magnetic field that is received via antennas.

A spatial encoding is superimposed on the signals with the aid of magnetic gradient fields, subsequently enabling the received signal to be assigned to a volume element. The received signal is then evaluated and a three-dimensional imaging visualization of the examination subject is provided. Local receive antennas, also known as local coils, may be used to receive the signals, which local coils are arranged directly on the examination subject in order to achieve a better signal-to-noise ratio.

A magnetic resonance tomography system permits a visualization of the interior of the body over a relatively long period of time, without exposing the patient or operator to an increased dose of ionizing radiation. However, it is not possible or only indirectly possible to detect instruments made of plastic or metal by magnetic resonance tomography. Additional systems including cameras and optical markers, for example, are known, though these represent considerable extra expenditure.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a method and a device that permit the instruments to be localized at minimal additional cost.

The instrument is provided for a medical examination or intervention using a magnetic resonance tomography system. The instrument may be a biopsy needle or a catheter or a surgical instrument, for example.

The instrument includes a transponder that is configured to emit a locator signal in a frequency range of the magnetic resonance tomography system. The emitting of the locator signal may be limited to the transmission of a supplied signal, provided by the magnetic resonance tomography system for example, by an antenna such as an inductive antenna loop or an electrical antenna, but may also include the generation of a signal by an oscillator and/or modulator in the transponder. A frequency which the magnetic resonance tomography system is able to pick up with its receivers is regarded as the frequency range of the magnetic resonance tomography system. This may be a Larmor frequency of a nuclear spin that is to be captured by the magnetic resonance tomography system or a frequency that lies in a frequency range of less than 100 kHz, 500 kHz, 1 MHz or 2 MHz around the Larmor frequency.

A plurality of transponders disposed on an instrument may be used, for example distributed over the dimensions of the instrument, in order for example to provide its orientation or contours to be visualized. A separation of the signals of the plurality of transponders may be achieved for example through the use of different frequencies or encoding schemes, as explained hereinbelow.

A locator signal in this context is a signal that may be received by the receivers of the magnetic resonance tomography system and that permits an evaluation for position determination purposes. This relates among other things to an amplitude of the locator signal that does not overmodulate the receivers, i.e., does not exceed a linear range of the receivers and thus permits a separate processing and subsequent separation of locator signal and magnetic resonance signal.

Different attenuations may be detected at the same time and used for position determination.

The locator signal includes an identifier by an encoding that permits it to be differentiated from magnetic resonance signals. Similarly, different encodings provide the signals of a plurality of transponders to be differentiated. Different encoding options are set forth hereinbelow in the dependent claims.

The identification of the locator signal by the encoding permits the locator signal to be separated from the magnetic resonance signal and sources of interference for the evaluation and, conversely, the locator signal to be suppressed in a magnetic resonance signal received by local coils to avoid artifacts.

The magnetic resonance tomography system includes a plurality of sensors for detecting a noise signal and a noise suppression device for suppressing noise signals in magnetic resonance signals received by the local coils. As sensors include in this context all antennas in the wider sense that are configured to detect alternating electric and/or magnetic fields in the already cited frequency range and forward them to the magnetic resonance tomography system or the noise suppression device for further processing. The sensors may include for example induction loops or electrical antennas, preamplifiers, filters, but also A/D converters. The sensors may be arranged in different predetermined positions around the patient tunnel or the field of view (FoV) in order to detect and differentiate noise signals from different directions. Not all the sensors may be arranged on a straight line or a plane, but instead are distributed three-dimensionally in space, i.e., at least one of the sensors is arranged outside of a plane with the other sensors. In other words, the sensors span a three-dimensional space.

By this arrangement of the sensors, however, it is possible to detect the locator signal by a plurality of sensors and to determine or triangulate the point of origin.

The noise suppression device is configured to reduce a noise signal, i.e., a signal that does not originate from the nuclear spins that are to be examined and is captured by the local coils or the bodycoil together with the magnetic resonance signal, in the signals of the local coil or bodycoil as a function of the signals of the sensors. This may be achieved for example in that the noise suppression device provides the signals with a phase shift and an attenuation and subtracts them from the signals of the local coils or the bodycoil. At the same time, the encoding for example permits the locator signal to be distinguished, and consequently to be separated, from the magnetic resonance signals and other noise signals. This also provides the locator signal to be interpreted as a noise signal and its effects on the magnetic resonance signal and the images produced therewith to be reduced.

The magnetic resonance tomography system additionally includes a location tracking device that is configured to pick up a locator signal of a transponder by the sensors. The location tracking device may receive the signals of the sensors in parallel with the noise suppression device and evaluates the signals. However, the noise suppression device may already have performed a source separation and thus already supplied the location tracking device with locator signal components of the sensors without magnetic resonance signal components or noise signal components. The location tracking device and the noise suppression device may use a common hardware platform, for example that is implemented also as software modules on collectively used processors.

The location tracking device is configured to determine a relative position of the transponder in relation to the sensors. In accordance with the inverse square law for electromagnetic fields, different amplitudes of the individual sensors may indicate a distance of the transponder from the respective sensor based on the attenuation. A phase of the signals and a signal delay associated therewith may also be used as distance information. The encoding provides phase information may go beyond the time limited to a whole period for the carrier wave and consequently permit greater distances and/or higher frequencies.

The noise suppression device may for example use these different paths between transponder and sensor for position determination via amplitude and phase in order to make the position identification more reliable and more accurate by error minimization.

The location tracking device may be implemented with neural networks that receive the signals of the sensors or the already separated signals from the noise suppression device as input values and from these, given predetermined positions of the sensors, determine the coordinates or the relative position. Training of the neural network may be performed with acquisition of the sensor data for predetermined positions of the transponder in the patient tunnel or FoV.

A neural network is able also to take into account complex propagation conditions due to reflection in the patient tunnel.

The encoding permits the sensors and the noise suppression device in cooperation with the location tracking device to provide a reliable localization of the transponder and consequently of the instrument by the existing elements of the magnetic resonance tomography system without degrading the image quality of the magnetic resonance tomography.

The method is a method for determining the relative position of a medical instrument with a magnetic resonance tomography system in relation to the magnetic resonance tomography system. The instrument is an instrument, as already described in the foregoing. The magnetic resonance tomography system is also a magnetic resonance tomography system, as described hereinabove.

In one step, an encoded locator signal is generated by the transponder. This may happen in different ways. The transponder may include for example an oscillator that generates a radiofrequency signal at a frequency in the frequency range, already presented in more detail, of the magnetic resonance tomography system. The encoding may for example already lie in the frequency of the radiofrequency signal in that, while it lies in the frequency range receivable by the magnetic resonance tomography system, it is at the same time outside of the frequencies of the nuclear spins during the image acquisition and consequently does not interfere with the image acquisition. The transponder may also include a modulator by which an encoding is modulated onto the radiofrequency signal of the oscillator. Encoding options are explained in more detail below. By the encoding it is possible to separate the locator signal from noise signals and magnetic resonance signals.

In an embodiment of the magnetic resonance system, the radiofrequency signal is supplied to the transponder by the magnetic resonance tomography system, for example via a signal line or wirelessly, instead of being generated locally by an oscillator. The locator signal may be derived locally from the supplied radiofrequency signal by dividers, multipliers or PLLs. This provides a defined frequency and/or phase relationship to be established that may be used for position determination. Also, because the parameters are known, the locator signal is then easier to suppress by the noise suppression device in a magnetic resonance signal received by the local coils.

In a step of the method, the locator signal is emitted by the transponder via an antenna. The antenna may be an inductive antenna such as an induction loop, for example, or an electrical antenna such as a monopole or dipole. The amplitude of the locator signal may be adjusted in advance by an attenuator or an amplifier in the transponder such that the locator signal does not overmodulate the receivers of the magnetic resonance tomography system via the sensors or local coils, i.e., it lies in the linear signal processing range of the receivers.

In a step of the method, the magnetic resonance tomography system receives the locator signal by the plurality of sensors. The sensors detect alternating electric and/or magnetic fields of the locator signal and forward the alternating electric and/or magnetic fields of the locator signal to the magnetic resonance tomography system. This may be accomplished in an analog manner following an optional filtering and/or amplification in the sensor. The forwarding may be realized in analog or digital form. The forwarded signal includes at least one item of information relating to amplitude, frequency and/or phase of the locator signal at the sensors, thereby providing a position of the transponder to be determined from the locator signal and the position of the sensors. The signal may be forwarded for evaluation to the receivers of the magnetic resonance tomography system or to the noise suppression device, or for example it is forwarded to the location tracking device.

In a step, the location tracking device separates the locator signal transmitted by the transponder from other signals such as magnetic resonance signals or noise signals. This may be accomplished for example with the aid of the encoding as follows. The location tracking device, in cooperation with or as a unit with the noise suppression device, may perform a source separation of the signals received from the sensors and the local coils. For example, the locator signal may be identified in the separated signals by the encoding.

The location tracking device determines a relative position of the transponder in relation to the sensors by the locator signals captured by the sensors. For this purpose, a location determination relation is applied to the locator signals. The term location determination relation in this context denotes a relation that uses the locator signal received from the sensors to determine a relative position of the transponder in relation to the sensors. Different ways are conceivable for this purpose. For example, an attenuation of the locator signal by way of the distance-dependent attenuation for electromagnetic fields may be used for triangulating the position of the transponder. Similarly, a time delay that may be determined by a phase shift of the carrier wave or an encoding modulated onto it may be used for triangulation by way of the time of flight. The different approaches may be combined in order to reduce the errors by an LSR algorithm, for example, in accordance with an overdetermined system. Also, for implementation of the location determination relation, a neural network may be used that receives the (as already described) preprocessed signals of the sensors as input values and as output values delivers the relative coordinates of the transponder. The network may be trained in that the sensor signals for predetermined positions of the transponder are acquired and supplied to the network. A deviation of the actual position from the position determined by the neural network may be used in this case for training the network e.g., by backpropagation.

The method shares the advantages of the magnetic resonance tomography system. In addition, for example a neural network enables a reliable position determination in a complex environment including multiple reflections in the patient tunnel.

In an embodiment of the instrument, the transponder has an energy source and an oscillator. The oscillator is in this case configured to generate the locator signal. The oscillator may have a quartz crystal oscillator, for example, or a radiofrequency generator stabilized in some other way.

This advantageously enables the transponder to be implemented without a line connection and its use simplified.

In an embodiment of the instrument, the encoding is a frequency encoding in a frequency range of the magnetic resonance tomography system. The locator signal is encoded by the frequency such that although it still lies in the receive range of the receivers of the magnetic resonance tomography system, at the same time it is not on a frequency that the magnetic resonance signal assumes during the image acquisition.

Advantageously, a mutual interference between image acquisition and location tracking of the transponder may be reduced in this way.

In an embodiment of the instrument, the encoding is a modulation by a pseudorandom code. By pseudorandom code is understood a signal or bit sequence that is not repeated within a predetermined period and for example is suitable for autocorrelation of a reference signal with a signal derived therefrom by transmission and permits a phase relationship or delay to be determined as a result of the transmission.

Advantageously, the pseudorandom code simplifies the detection of the locator signal by autocorrelation and as a result the separation of the signals and the determination of signal delays. Given a plurality of transponders, different pseudorandom codes may also be used for separating the signals of the different transponders. The different pseudorandom codes may be orthogonal to one another so that the respective transponder signal may be selected by convolution with a pseudorandom code.

In an embodiment of the instrument, the transponder is configured to receive the locator signal from the magnetic resonance tomography system and to emit the signal. It is conceivable in this case that the locator signal, or preferably a base frequency from which the locator signal is derived by dividers, multipliers or PLLs, is supplied to the transponder via the line or wirelessly by the magnetic resonance tomography system.

Thus, a perturbation of the magnetic resonance tomography system due to the oscillator signal may advantageously be prevented and an evaluation of the locator signal simplified as a result of the fixed frequency and phase relationship. Owing to the fixed relationship between the locator signal and the signal that is transmitted to the transponder by the magnetic resonance system, the locator signal may also be more easily suppressed in the received magnetic resonance signals by the noise suppression device on the basis of this information.

A system includes an instrument and a magnetic resonance tomography system. Advantageously, the location tracking device of the magnetic resonance tomography system is configured to separate the locator signal of the transponder of the instrument from the noise signals by the encoding.

In an embodiment of the method, the method further includes the step of arranging the transponder or the instrument having the transponder at a predetermined relative position in relation to the sensors. The predetermined relative position may be in an operating range of the instrument as per application, for example in the FoV of the magnetic resonance tomography system or in a directly adjacent extended region that may still be imaged by the magnetic resonance tomography system.

In a step, the location determination relation is calibrated or corrected with the aid of the predetermined relative position and the determined relative position such that the result of the location determination relation for the locator signal of the transponder at the predetermined position deviates less from the predetermined relative position of the transponder.

The steps of positioning the transponder at a predetermined position and the ensuing calibration of the location determination relation by a plurality of different predetermined positions, for example distributed over the FoV, may be repeated.

The accuracy of the position determination may be improved as a result. If the location determination relation is implemented as a neural network, then the neural network may also be trained in this way.

In an embodiment of the method, the method includes the step of detecting a position of the instrument in a magnetic resonance acquisition by the transponder. This may be accomplished for example by the instrument or the transponder having a marking with a magnetic resonance-active substance or an active resonance element on the Larmor frequency. An indirect imaging of the instrument or of the transponder may be used if these cause an impact on the imaging of the environment.

In a step, the magnetic resonance acquisition is then calibrated or corrected as a function of the position of the transponder detected in the magnetic resonance acquisition and the position of the transponder detected by the tracking.

A position determination by the locator signal is independent of errors in the homogeneity of the static magnetic field or distortions due to eddy currents and thus offers a correction option that is independent thereof.

The above-described characteristics, features and advantages, as well as the manner in which these are realized, will become clearer and more readily understandable in connection with the following description of the embodiments, that are explained in more detail with reference to the drawings, in which:

DETAILED DESCRIPTION

Figure 1:
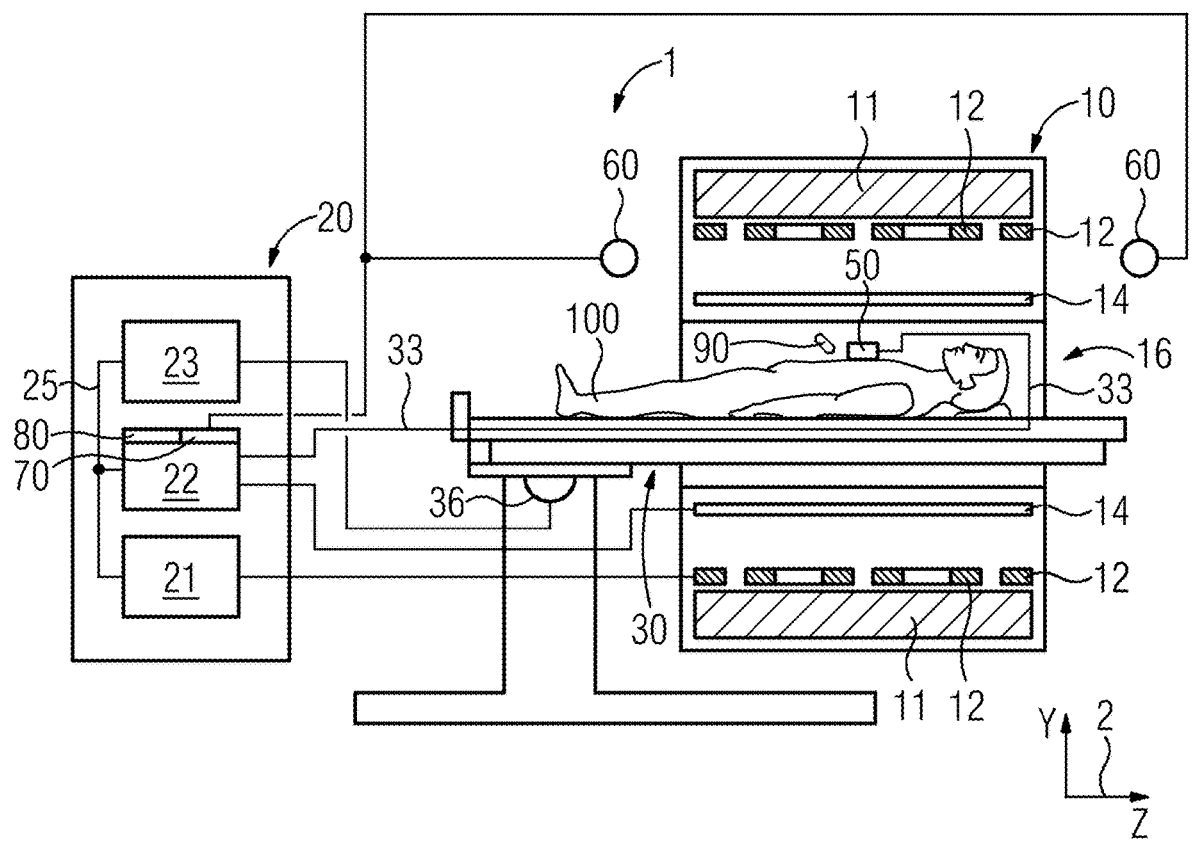
FIG. 1 depicts a schematic representation of a magnetic resonance tomography system with an instrument according to an embodiment.

FIG. 1 depicts a schematic representation of an embodiment of a magnetic resonance tomography system 1 for performing the method.

The magnet unit 10 includes a field magnet 11 that generates a static magnetic field B0 for aligning nuclear spins of specimens or of the patient 100 in an acquisition region. The acquisition region is characterized by an extremely homogeneous static magnetic field B0, the homogeneity relating for example to the magnetic field strength or the absolute value. The acquisition region is virtually spherical in shape and is arranged in a patient tunnel 16 that extends in a longitudinal direction 2 through the magnet unit 10. A patient couch 30 may be moved in the patient tunnel 16 by the positioning unit 36. Typically, the field magnet 11 is a superconducting magnet that is able to provide magnetic fields having a magnetic flux density of up to 3 T, even higher in the case of the latest devices. For lower magnetic field strengths, however, permanent magnets or electromagnets with normally conducting coils may also find application.

In addition, the magnet unit 10 has gradient coils 12 that are configured to overlay the magnetic field B0 with temporally and spatially variable magnetic fields in three spatial directions in order to spatially differentiate the acquired imaging regions in the examination volume. The gradient coils 12 are typically coils composed of normally conducting wires that may generate fields orthogonal to one another in the examination volume.

The magnet unit 10 also includes a bodycoil 14 that is configured to radiate a radiofrequency signal supplied via a signal line into the examination volume and to receive resonance signals emitted from the patient 100 and pass them on via a signal line.

A control unit 20 supplies the magnet unit 10 with the different signals for the gradient coils 12 and the bodycoil 14 and evaluates the received signals.

The control unit 20 includes a gradient controller 21 that is configured to supply the gradient coils 12 via feeder lines with variable currents that provide the desired gradient fields in the examination volume in a coordinated manner with respect to time.

The control unit 20 additionally includes a radiofrequency unit 22 that is configured to generate a radiofrequency pulse having a predefined time characteristic, amplitude and spectral power distribution in order to excite a magnetic resonance of the nuclear spins in the patient 100. Pulse powers in the kilowatt range may be achieved in this case. The excitation signals may be radiated into the patient 100 via the bodycoil 14 or also via a local transmit antenna.

A controller 23 communicates with the gradient controller 21 and the radiofrequency unit 22 via a signal bus 25.

Sensors 60 are connected to a noise suppression device 70. The sensors 60 may be arranged in different spatial directions relative to the field of view of the magnetic resonance tomography system 1 such that the sensors 60 span a three-dimensional coordinate system. For example, three or more sensors 60 may be distributed as shown along the circumference of the openings of the patient tunnel. Sensors 60 may be located at the two opposite openings of the patient tunnel 16 in order to permit a better location determination along the z-axis between the openings. The sensors 60 are for example induction loops that detect alternating magnetic fields and forward them to the radiofrequency unit 22 via signal connections 61. A noise suppression device 70 and location tracking device 80 are provided in the radiofrequency unit 22 in order to receive and process the signals from the sensors 60.

The noise suppression device 70 and the location tracking device 80 may be implemented in this case on a common piece of hardware, for example a signal processor, as a software module or as an FPGA. However, the noise suppression device 70 and the location tracking device 80 may have only parts of the signal processing in common or are configured completely separately. Details concerning the noise suppression device 70 and the location tracking device 80 are presented in more detail below with reference to FIG. 2.

An instrument 90 is located in the patient tunnel and from there transmits a locator signal by the transponder 92, which locator signal is detected by the sensors 60.

Figure 2:
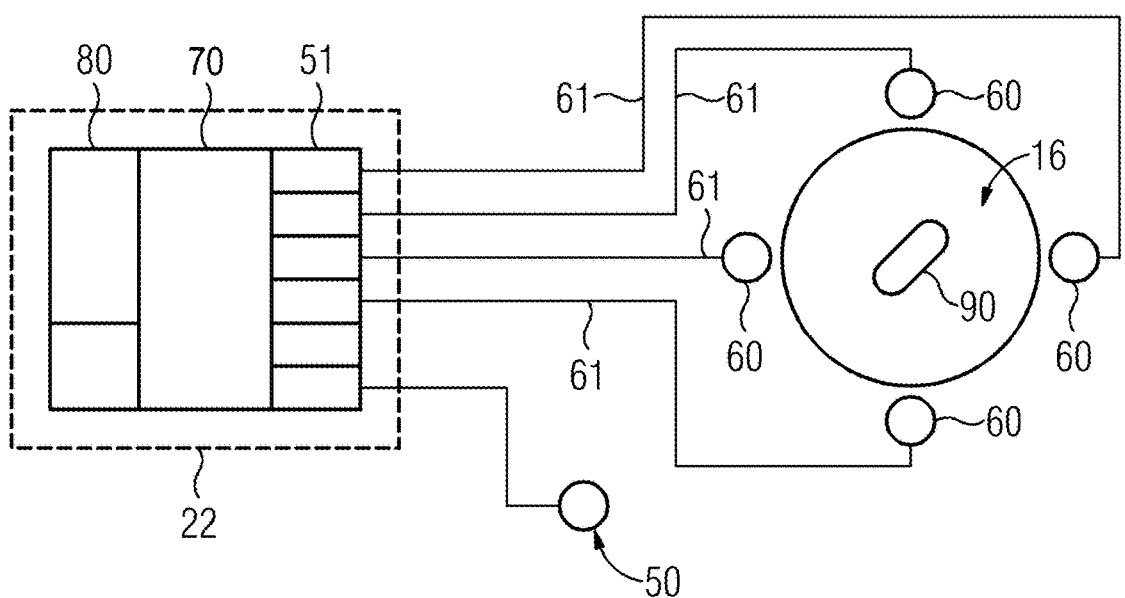
FIG. 2 depicts a schematic representation of a radiofrequency unit of a magnetic resonance tomography system according to an embodiment.

FIG. 2 depicts a schematic representation of a radiofrequency unit 22 of a magnetic resonance tomography system 1 including a location tracking device 80 and a noise suppression device 70 as well as the sensors 60 and the instrument 90. Like objects are labeled with the same reference signs.

The sensors 60 are arranged around the opening of the patient tunnel 16, where the sensors 60 receive the locator signal of the instrument 90 or of its transponder 92. The signals of the sensors 60 are forwarded to the radiofrequency unit 22 via the signal connections 61. At the radiofrequency unit 22, the signal is processed by receivers 51, for example amplified, filtered and, if this has not already happened in the sensor 60, also digitized. The receivers 51 may be receivers that are also used for conditioning the signals of the local coils 50 for image acquisition. The preprocessed signals of the sensors 60 are supplied to the location tracking device 80 and/or the noise suppression device 70 by the receivers 51.

The noise suppression device 70 is configured to detect electromagnetic perturbations by the sensors 60 and to reduce destructive interference in the magnetic resonance signals captured by the local coil 50. A source separation algorithm, among other things, may be used that may then also separate the signals of the sensors 60 according to the different sources, such as, for example, the locator signal and the sources of interference, that simplifies the following evaluation of the locator signal. The locator signal of the transponder 92 also potentially represents a noise signal for the magnetic resonance signal such that the noise suppression device 70 may use a locator signal detected by the location tracking device 80 in order to suppress the locator signal in the magnetic resonance signals captured by the local coil 50 more effectively by the noise suppression device 70.

The location tracking device 80 may at the same time evaluate the signals of the sensors 60 in different ways. For example, phase differences between the individual signals may be evaluated as time-of-flight differences and consequently as distances of the sensors 60 from the transponder 92. The phase shift of a modulated may be encoded as a function of the frequency of the locator signal instead of the carrier wave itself in order to provide times of flight greater than a period of the frequency of the locator signal to be detected. Pseudorandom sequences that may be evaluated in the location tracking device by cross-correlation or autocorrelation by a correlator are suitable as an encoding option, for example. A pseudorandom sequence also provides a signal below the noise threshold to be detected and evaluated by the correlator and thus the perturbations of the magnetic resonance signal to be minimized.

A different amplitude of the sensor signals may also be converted into a distance value as a distance-dependent attenuation of alternating electric and/or magnetic fields. The position of the transponder 92 may be determined based on the determined distances of the transponder 92 from the sensors 60. The error may be reduced for example if the transponder 92 is arranged between the sensors 60, i.e., is enclosed by a polygon having sensors 60 on the vertices.

The location determination may be accomplished by a location determination relation that receives the locator signals received from the sensors 60 as input values and as output value yields the coordinates of the relative position of the transponder 92 in relation to the sensors 60 and consequently to the magnetic resonance tomography system 1. An analytical solution using four sensors may be used. A greater number of sensors 60 delivers an overdetermined system that represents for example an optimization problem that allows a more accurate and more reliable position determination by an error minimization method such as least square root (LSR). Different results from amplitude and time of flight may also be used in this overdetermined system in order to further improve the position determination.

The location determination relation may be implemented by a neural network. The neural network may be trained in this case by training data obtained by acquiring the signals of the sensors 60 for respective predetermined training positions of the transponder 92. The relative positions determined by the neural network from the sensor signals are compared with the predetermined training positions and the deviations are reduced by backpropagation.

Figure 3:
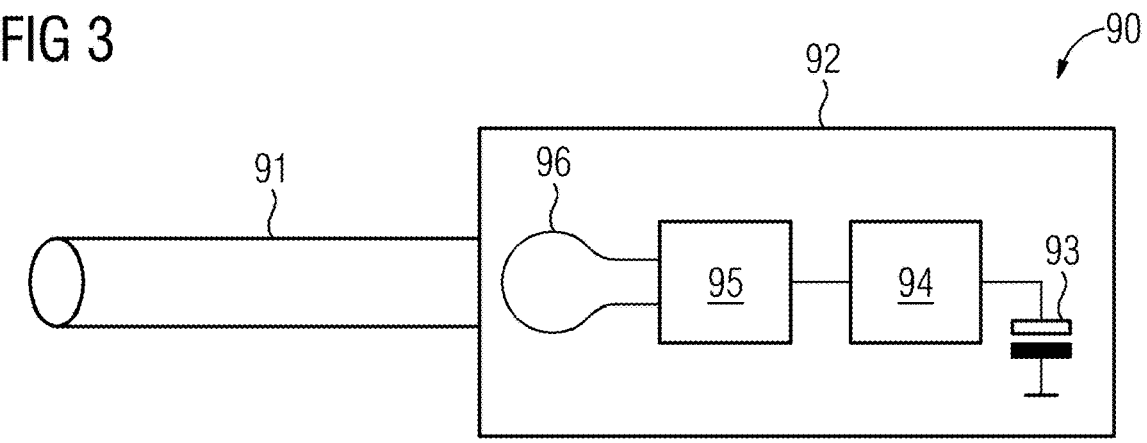
FIG. 3 depicts a schematic representation of an instruments according to an embodiment.

FIG. 3 depicts a possible embodiment of an instrument. A transponder 92 is arranged on a surgical instrument such as a biopsy needle 91, for example. The transponder 92 has an energy source 93, for example a battery or a rechargeable storage battery. A wireless energy supply via induction is also conceivable. The energy source 93 supplies the components of the transponder 92 with power.

An oscillator 94 generates a high-frequency alternating current having a frequency preferably in a receive range of the receivers of the magnetic resonance tomography system 1 for the magnetic resonance signal. The high-frequency alternating current is modulated by a modulator 95 by an encoding that is configured to make the locator signal distinguishable from magnetic resonance signals and/or noise signals. The encoding may include time information for time-of-flight detection. The locator signal is subsequently emitted by a transmit antenna 96, for example an induction coil.

The transponder 92 may not generate the radiofrequency signal independently, but instead the signal is derived from a signal transmitted to the transponder 92 by the magnetic resonance tomography system 1 via a hardwired or wireless connection. The locator signal may be generated therefrom for example by a frequency multiplier, frequency divider or PLL. In this way, a fixed frequency and phase relationship in relation to the magnetic resonance signals may advantageously be ensured that enables an interfering interaction with the magnetic resonance signals to be reduced. The effect of the noise suppression device 70 is also better if, as in the case of a locator signal generated by the magnetic resonance tomography system 1, the characteristics are precisely known.

Figure 4:
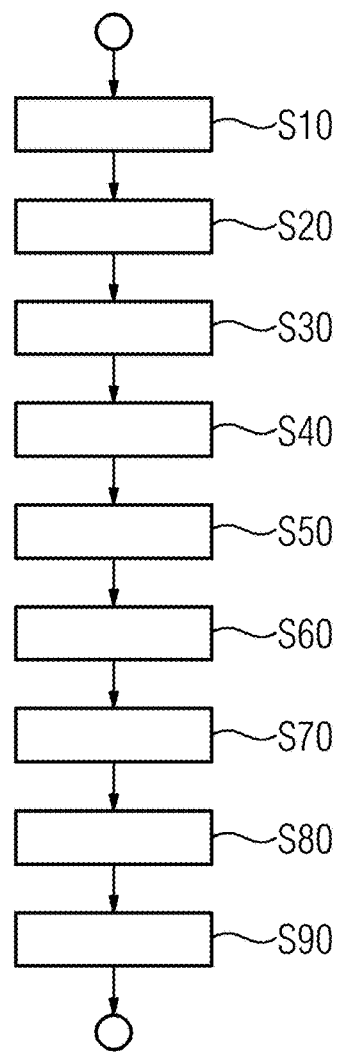
FIG. 4 depicts a schematic flowchart of an embodiment of a method.

FIG. 4 depicts a schematic flowchart of an embodiment of a method.

In a step S20, an encoded locator signal is generated by the transponder 92, as already explained with reference to FIG. 3.

In a step S30, the encoded locator signal is transmitted by the transponder 92, for example via its transmit antenna 96.

In a step S40, the locator signal emitted by the transponder is detected or received by the plurality of sensors 60. In this case the receiving may also include a preprocessing of the received signals by amplifiers, filters, frequency converters and/or A/D converters. Some of the preprocessing may in this case also be performed in the receivers 51 of the magnetic resonance tomography system 1.

In another step S50, the locator signal is separated from further signals received by the sensors 60 by the location tracking device 80 and/or the noise suppression device 70.

In a further step S60, a relative position of the transponder 92 in relation to the sensors 60 is determined by the location tracking device 80 by the locator signal detected by the sensors 60 and a location determination relation applied thereto. An attenuation or time of flight of the locator signal may be used for determining the distance between transponder 92 and the respective sensors 60. A processor of the location tracking device 60 may determine a relative position of the sensor with the smallest possible error therefrom, for example via an optimization problem. The implementation of the location determination relation may also be implemented by a neural network.

In an embodiment of the method, the location tracking device is calibrated, or the neural network trained in a step S10 by positioning the transponder 92 at a predetermined relative position in relation to the sensors 60. According to steps S20 to S60, a relative position of the transponder 92 is determined by the location tracking device 80 and in a step S70 the location determination relation is calibrated or trained with the aid of the predetermined relative position and the determined relative position.

In an embodiment of the method, a magnetic resonance acquisition is calibrated with the aid of the location tracking device. In a step S80, a position of the instrument 90 is detected by the transponder 92 in a magnetic resonance acquisition. The instrument 90 may include a marker that becomes visible in an acquired magnetic resonance image, for example an active substance or an electrical resonator on the Larmor frequency. Imaging due to artifacts generated by the instrument in an environment is also conceivable.

Next, in a step S90, the magnetic resonance acquisition or the image reconstruction of the magnetic resonance tomography system is calibrated or corrected by comparison of the relative position detected by the location tracking device from steps S20 to S60 with the position in the acquired magnetic resonance image.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a relative position of a medical instrument with a magnetic resonance tomography system, wherein the instrument includes a transponder configured for transmitting a locator signal, the magnetic resonance tomography system comprises a plurality of sensors configured for detecting noise signals including the locator signal, wherein the noise signals are used for active noise cancelling for the magnetic resonance tomography system, the plurality of sensors in signal connection with a location tracking device, the method comprising:
   encoding, by the transponder, the locator signal in a frequency range of the magnetic resonance tomography system;
   emitting the encoded locator signal by the transponder;
   receiving a plurality of signals by the plurality of sensors, wherein the plurality of sensors are positioned outside an opening of a patient tunnel of the magnetic resonance tomography system;
   separating the encoded locator signal from magnetic resonance signals and other noise signals in the plurality of signals received by the plurality of sensors;
   determining the relative position of the instrument in relation to the plurality of sensors by the location tracking device by the encoded locator signal and a location determination relation applied thereto.

2. The method of claim 1, further comprising:
   positioning the transponder at a predetermined relative position in relation to the plurality of sensors; and
   calibrating the location determination relation using the predetermined relative position and the determined relative position.

3. The method of claim 1, further comprising:
   detecting a position of the instrument in a magnetic resonance acquisition by the transponder; and
   calibrating the magnetic resonance acquisition as a function of the position detected in the magnetic resonance acquisition and the relative position determined by the location tracking device.

4. The method of claim 1, further comprising:
   separating the other noise signals from the magnetic resonance signals in the plurality of signals received by the plurality of sensors; and
   reducing destructive interference in the magnetic resonance signals captured by a local coil of the magnetic tomography system by suppressing the encoded locator signal and the noise signals.

5. The method of claim 1, wherein the encoding of the encoded locator signal is a frequency encoding in a frequency range of the magnetic resonance tomography system, wherein the plurality of sensors are configured to detect alternating electric and/or magnetic fields in the frequency range.

6. The method of claim 1, wherein the encoding of the encoded locator signal is a modulation by a pseudorandom code.

7. A magnetic resonance tomography system comprising:
   a plurality of local coils configured to receive magnetic resonance signals;
   a transponder coupled with an instrument, the transponder configured to encode a locator signal and transmit the encoded locator signal in a frequency range of the magnetic resonance tomography system;
   a plurality of sensors configured for detecting noise signals including the encoded locator signal, wherein the noise signals are used for active noise cancelling for the magnetic resonance tomography system, wherein the plurality of sensors are positioned outside an opening of a patient tunnel of the magnetic resonance tomography system;
   a location tracking device configured to separate the encoded locator signal from other noise signals with the aid of the encoding of the locator signal, the location tracking device configured to determine a relative position of the instrument in relation to the plurality of sensors using the encoded locator signal and a location determination relation applied thereto; and
   a noise suppression device configured to separate the noise signals from the magnetic resonance signals received by the plurality of local coils, the noise suppression device configured to reduce destructive interference in the magnetic resonance signals by suppressing the noise signals including the encoded locator signal.

* * * * *